United States Patent
Geistert et al.

(10) Patent No.: US 9,167,966 B2
(45) Date of Patent: Oct. 27, 2015

(54) DISSIPATION DEVICE AND MRI-SAFE CATHETER SYSTEM

(75) Inventors: Wolfgang Geistert, Rheinfelden (DE); Erhard Flach, Berlin (DE); Ingo Weiss, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 210 days.

(21) Appl. No.: 13/089,774

(22) Filed: Apr. 19, 2011

(65) Prior Publication Data

US 2011/0263966 A1      Oct. 27, 2011

(30) Foreign Application Priority Data

Apr. 26, 2010   (EP) .................................... 10161071

(51) Int. Cl.
*A61B 5/00* (2006.01)
*A61N 1/05* (2006.01)
*A61N 1/08* (2006.01)
*G01R 33/28* (2006.01)

(52) U.S. Cl.
CPC ... *A61B 5/00* (2013.01); *A61N 1/05* (2013.01); *A61B 2562/182* (2013.01); *A61N 2001/086* (2013.01); *G01R 33/288* (2013.01)

(58) Field of Classification Search
USPC .......... 600/411, 423, 427, 433–435, 466–467
See application file for complete search history.

(56) References Cited

U.S. PATENT DOCUMENTS

| | | | | |
|---|---|---|---|---|
| 3,653,851 | A * | 4/1972 | Gruber | 428/539.5 |
| 4,158,142 | A * | 6/1979 | Haimson | 378/10 |
| 6,971,391 | B1 * | 12/2005 | Wang et al. | 128/846 |
| 2002/0198520 | A1 * | 12/2002 | Coen et al. | 606/41 |
| 2004/0210289 | A1 * | 10/2004 | Wang et al. | 607/116 |
| 2004/0225213 | A1 * | 11/2004 | Wang et al. | 600/421 |
| 2007/0108195 | A1 * | 5/2007 | Tian et al. | 219/702 |
| 2010/0174349 | A1 * | 7/2010 | Stevenson et al. | 607/116 |

* cited by examiner

*Primary Examiner* — Joel F Brutus
(74) *Attorney, Agent, or Firm* — Buchanan Ingersoll & Rooney PC

(57) ABSTRACT

A dissipation device having a proximal end, which is located outside the body, and a distal end, which is suited in particular for elongate medical instruments, in particular electrophysiological catheters or temporary electrode leads, placed temporarily in the body. The dissipation device including a dissipation sleeve which extends from the proximal end to the distal end of the dissipation device, and a lumen which extends from the proximal end to the distal end, and in which the instrument can be displaceably guided, wherein the lumen is enclosed by the dissipation sleeve. The dissipation device is characterized in that the dissipation sleeve is composed, at least partially, of electrically conductive material, and/or the dissipation sleeve includes dissipation means composed of electrically conductive material and, therefore, the dissipation sleeve is designed to dissipate or divert electrical energy induced by electromagnetic radiation.

20 Claims, 7 Drawing Sheets

DISSIPATION DEVICE AND MRI-SAFE CATHETER SYSTEM

CROSS-REFERENCE TO RELATED APPLICATIONS

The present application claims the priority of European Patent Application No. 10161071.5, filed on Apr. 26, 2010 in the European Patent Office, the disclosure of which is hereby incorporated by reference in its entirety.

TECHNICAL FIELD

The present invention relates to a dissipation device for elongate medical instruments located temporarily in the body, and additionally to a system for treating the human body, which is comprised of a dissipation device and an elongate medical instrument.

BACKGROUND

In recent years, magnetic resonance ("MR") diagnostic devices, which are also referred to below as MR devices (e.g., magnetic resonance tomograph=MRT), have become particularly significant due to their examination methodology, which is gentle on the patient, non-invasive, and entirely pain-free and without side effects. Typical medical implants comprised of conductive materials, which also include electrophysiological catheters and/or known intracardial electrodes implanted temporarily or permanently for intervention purposes, have the problem that they heat up considerably in magnetic resonance diagnostic devices under the influence of the electromagnetic radiation generated thereby, and also due to the emission of the induced energy in the region of their contact surface(s) with tissue, i.e., electrode poles which are designed as ring electrodes and tip electrodes. The reason therefore, in particular, is the solid metallic supply leads to the contact surfaces, which function as antennas; due to the insulation thereof, the antenna currents induced by high-frequency ("HF") fields are diverted into the body electrolytes only at the contact surfaces that form the electrical boundary surface with the tissue. The aforementioned HF fields function in a working frequency range, for instance, of 21 MHz in the case of a 0.5 tesla MR tomograph. According to the current state of the art, the working frequency range can reach up to 300 MHz for a 7 tesla MR tomograph, and is typically 64 MHz for a 1.5 tesla MR tomograph. Since the tissue in the vicinity of the electrode pole(s) can become heated to an extreme extent, minimally invasive catheter ablations cannot be performed using magnetic resonance imaging.

To prevent or minimize the dangerous heating of the body cells, the maximum antenna current must be limited or reduced. Known solutions primarily in the field of intracardial electrode leads provide discrete components which function as band-stop filters or low-pass filters and, thereby, limit the lead resistance of the antenna for the frequencies of interest. Other known solutions provide capacitors which are connected in parallel to the insulation and, thereby, dissipate the antenna current.

Example documents in this regard are U.S. Pat. No. 6,944,489, U.S. Publication No. 2003/0144720, U.S. Publication No. 2003/0144721, and U.S. Publication No. 2005/0288751 (and the parallel documents U.S. Publication No. 2005/0288752, U.S. Publication No. 2005/0288754, and U.S. Publication No. 2005/0288756, which comprise substantially identical wording and were published in parallel).

Basically, it is possible to influence the inductance and capacitive coupling of the antenna using design measures, and to thereby reduce the flow of antenna current, dissipate the same, or shift the resonant frequency. The design requirements on a medical instrument of the initially described type, which are important in terms of therapy, typically permit very little leeway in this regard, however.

Furthermore, in contrast to the highly simplified consideration examined herein, antennas also have further resonant frequencies, and so shifting the resonant behavior of the electrode may fulfill the resonant condition of an MR device having other HF frequencies. This approach is therefore not advantageous.

Document EP 0 884 024, which is also referenced as technological background, discloses the case of which a capacitor is connected between the supply leads for the ablation pole of a catheter and a measurement pole which is also disposed thereon and is used to receive EKG signals. Due to the capacitor, high-frequency energy can be delivered via the ablation electrode to perform ablation, and an EKG signal can be received at the same time.

The disclosed dissipation device and system are directed at overcoming one or more of the above-identified problems.

SUMMARY

Proceeding from this prior art, the problem addressed by the present invention is that of making a medical instrument—in particular, an electrophysiological catheter or a temporarily implantable electrode lead—usable even in radiation fields of MR diagnostic devices without making any, or minimal, design changes, and without any, or minimal, relevant risk to the carrier. This should take place, in particular, by using materials which can be manufactured easily and at low cost, and which permit the properties of the electrode(s) with respect to the antenna characteristics thereof to become diminished in a specific, effective, and sufficient manner, without causing current concentrations and related excessive heating at electrical functional points of the medical implant, in particular, at contact points with the surrounding body.

This problem is solved according to the claims by a dissipation device having a proximal end, which is located outside the body, and a distal end, which is suited, in particular, for elongate medical instruments placed in the body temporarily, in particular, electrophysiological catheters or temporary electrode leads. The dissipation device comprising a dissipation sleeve which extends from the proximal end to the distal end of the dissipation device, and a lumen which extends from the proximal end to the distal end, and in which the instrument can be displaceably guided, wherein the lumen is enclosed by the dissipation sleeve. According to the present invention, the dissipation device is characterized in that the dissipation sleeve is comprised, at least partially, of an electrically conductive material, and/or the dissipation sleeve comprises a dissipation means comprised of an electrically conductive material and, therefore, the dissipation sleeve is designed to dissipate or divert electrical energy induced by electromagnetic radiation. In one embodiment, the dissipation sleeve could comprise an inner layer (a "liner") which is non-conductive. This inner layer can extend in sections from the proximal end to the distal end, or can be only a piece on the distal end or proximal end.

Due to this simple structural solution, according to the present invention, the quality of the oscillating circuit formed by the medical instrument with the body together as an antenna, is reduced by the dissipation to the extent that the energy absorbed by the antenna is reduced and the losses in the entire scheme of instrument/insulation/body are distributed such that excessive current concentration does not occur at certain points; this will become clear in the subsequent description of the background of the invention within the scope of the description of the various embodiments.

The main advantage of the reduction in the quality of the antenna compared to a band filter is that the method of operation is dependent upon the resonant frequency of the antenna and the frequency of the incident electromagnetic alternating field, i.e., the energy absorbed by the antenna is reduced at all frequencies. In this manner, the solution according to the present invention operates identically with different MR devices having different working frequencies.

Various other objects, aspects and advantages of the present invention can be obtained from a study of the specification, the drawings, and the appended claims.

DETAILED DESCRIPTION

As the background of the invention, the following basic embodiments of the oscillation behavior of antenna circuits shall first be presented:

If a preferably elongate, electrical conductor is located in a room, said conductor functions as an antenna for electromagnetic radiation which passes through the room. The antenna converts the free-space wave into a transverse electromagnetic wave, thereby enabling antenna currents to flow. This situation occurs, for instance, when a patient is treated in an MR diagnostic device using electrophysiological ablation catheters, which can be inserted in a minimally invasive manner. The currents that are produced during this treatment in the electrophysiological catheter, which functions as an antenna, are directed into the body at the contact points with the body tissue—at the electrode poles in this case—where they are converted mainly into heat. Depending on the strength of the electromagnetic alternating field, the extent of the heating can be dangerous to the patient.

Figure 1:
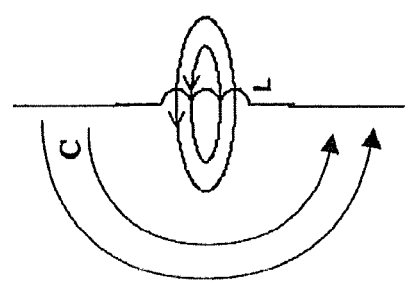
FIG. 1 shows a schematic diagram to illustrate the simplified operating principle of an antenna as an open oscillating circuit.
Figure 1:
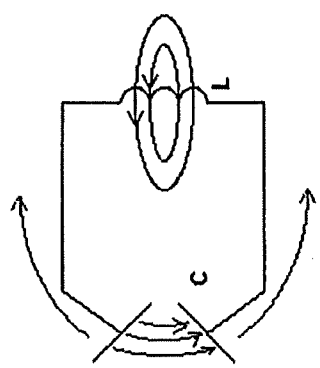

In a simplified representation, an antenna is an open oscillating circuit, which can be understood by imagining that the capacitor plates of a closed oscillating circuit are pulled apart into an elongated shape (see FIG. 1). In this simplified depiction, the antenna rod represents an inductor L, the ends of which are capacitively coupled to each other (capacitance C). The antenna current reaches its maximum amplitude when resonance is present, i.e., when the oscillating circuit is driven at the resonant frequency $f_0$. The resonant frequency of the oscillating circuit depicted in FIG. 1 is:

$$f_0 = \frac{1}{2\pi\sqrt{LC}}.$$

Figure 3:
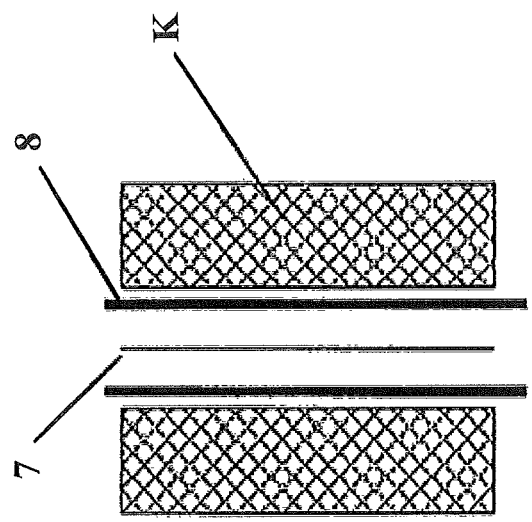
FIG. 3 shows a schematic representation of a medical instrument, such as an electrophysiological catheter or a temporary electrode lead, comprising a supply lead and an electrode sheath, in the physical surroundings thereof.
Figure 2:
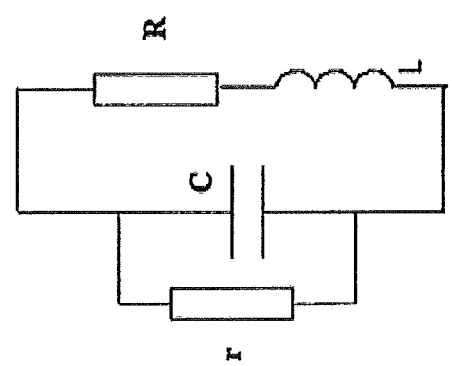
FIG. 2 shows an equivalent circuit diagram of a medical instrument as an oscillating circuit with resistive losses.

In reality, components L and C incur losses, i.e., the inductor has a series-connected ohmic resistance R, while the capacitance is an ohmic resistance r connected in parallel (see FIG. 2). In the case of an electrophysiological catheter, the shaft section of which is shown in FIG. 3, a supply lead 7 is the antenna rod for high-frequency signals or measurement signals, for instance. The antenna rod has an inductance L and lead resistance R, which are dependent on the geometry and the material properties. The capacitive coupling of the remote lead sections takes place via the surrounding dielectric medium (which includes a catheter insulation 8 and body K of the patient to be treated). Ohmic losses of the insulation and the body are summarized in the equivalent circuit diagram depicted in FIG. 2 by resistor r. For the function of the electrophysiological catheter, the objective for ablation, as well as the measurement of electrophysiological signals at the treatment site, is for supply lead 7 to conduct as well as possible in the longitudinal direction (that is, resistance R is as small as possible), but for insulation 8 to be as good as possible (that is, resistance r is as great as possible). The resistive components affect the quality Q of the oscillating circuit, which is a measure of how high the antenna currents can get for a given intensity of electromagnetic radiation. The quality is calculated as the quotient:

$$Q = \frac{f_0}{B},$$

where $f_0$ is the resonant frequency and B is the bandwidth. The bandwidth is defined by the limiting frequencies (f=f1, f=f2), beyond which the level of conductivity |$\underline{Y}$| drops below $1/\sqrt{2}$ of the maximum value.

In the case of the oscillating circuit depicted in FIG. 2:

$$|Y| = \left| \frac{1}{R + j2\pi fL + \frac{1}{1/r + j2\pi fC}} \right|, (j = \sqrt{-1}).$$

The quality of the oscillating circuit (and therefore the maximum possible antenna current) is particularly good for known electrophysiological catheters, i.e., it increases as R decreases and r increases. This occurs, in particular, during resonance. Due to the physiologically required length of the catheter (of approximately 50 to 130 cm), the dielectric properties of the body and, furthermore, the conventional design, the resonance condition occurs very close to the Larmor frequency for hydrogen of approximately 64 MHz in 1.5 T MR devices. Using an inductance, as an example, of typically 3 µH of the electrode lead, and a capacitance of approximately 2 pF, the resonance frequency of the oscillating circuit under consideration is $f_0$=64.97 MHz.

Figure 4:
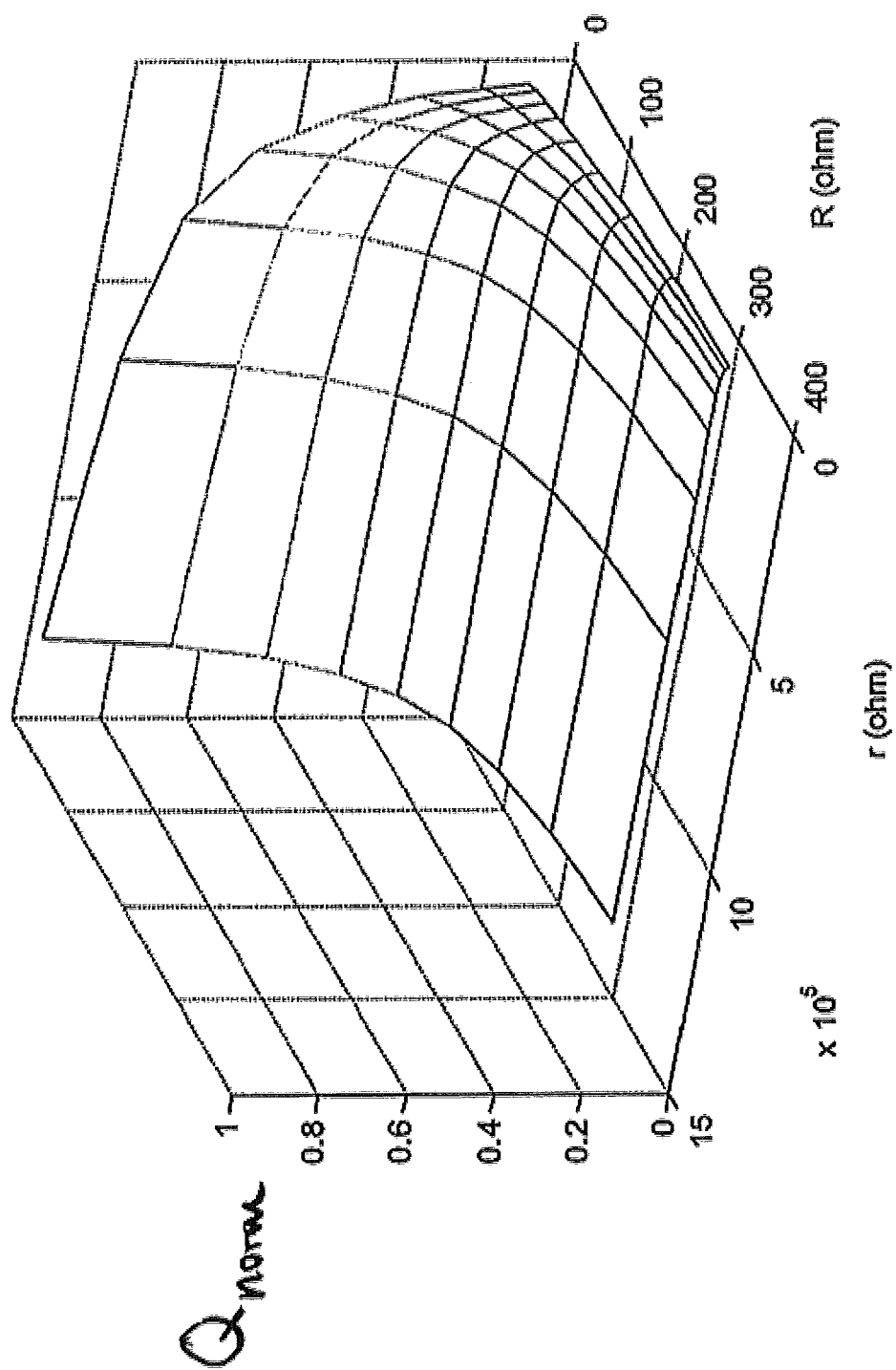
FIG. 4 shows a diagram for illustrating the dependence of the normalized oscillating-circuit quality on the ohmic resistance components of the capacitance and inductance of the equivalent circuit diagram-oscillating circuit according to FIG. 3.

For purposes of illustration, FIG. 4 shows the dependence of the quality of the loss-prone oscillating circuit depicted in FIG. 2 on ohmic loss resistances R and r within practical value ranges, assuming L=3 µH and C=2 pF. In terms of quality, the configuration of this dependence is also similar for L and C values that deviate greatly there from.

As shown in FIG. 4, the quality of the antenna can be reduced, advantageously, by reducing the resistance r of the antenna sheath, increasing the resistance R of the antenna lead, or by implementing both measures. This means that the antenna properties can be influenced such that current concentrations do not occur in the radiation fields and, therefore, neither does excessive heating at the electrode poles. In the case of intracardial electrodes, it is therefore known that these means are to reduce the quality of the oscillating circuit formed by the electrode together with the body as an antenna to the extent that the energy received by the antenna is reduced and the losses in the entire scheme of instrument/insulation/body are distributed such that excessive current concentration does not occur at certain points.

Therefore, in the case of electrophysiological catheters, the usual electrode insulation can be replaced with a low-insulating material in order to reduce the sheath resistance of the electrode lead toward the body, to lower the quality of the antenna, and to minimize the antenna currents induced in the electrode lead and, therefore, the induced heating in the presence of electromagnetic alternating fields.

It is also possible, according to the prior art, to increase the lead resistance of the electrode lead.

To increase the effectiveness, the two solutions described above can be optimally combined, i.e., decrease the sheath resistance of the electrode sheath and increase the lead resistance of the electrode lead, thereby reducing the quality to the best extent possible, as depicted in FIG. 4. This approach is particularly suited for cardiac pacemaker electrodes and neurostimulation electrodes, as known from U.S. Publication No. 2006/0200218.

These two solutions from the field of intracardial electrode leads are not, however, always suitable for medical instruments of the initially described type. Such instruments are usually not designed to permit extensive structural changes. This can be due to size, or due to the fact that it is not possible to integrate filter means, for instance. Electrophysiological catheters are examples of this situation. Such catheters must be easy to control. This means, there is little space available for increasing the lead cross section, for instance, or varying the thickness of the insulation. Both would unavoidably result in a stiffening of the shaft and therefore the controllability of the catheter.

The present invention will be described in the following with reference, for example, to an electrophysiological catheter—also referred to below as a deployment catheter—as the medical instrument. One skilled in the art will appreciate that other elongate medical instruments may be utilized without departing from the spirit and scope of the present invention.

In the solution according to the present invention, in addition to the deployment catheter, an outer catheter (dissipation device or "sheath") is also provided, which is slid over the deployment catheter.

However, the sheath according to the invention comprises a dissipation sleeve or a dissipation means comprised of electrically conductive material which prevents or reduces the energy absorption from the HF field by long, low-resistance structures of the deployment catheter. Preferably, the dissipation sleeve or the dissipation means can also be comprised entirely of electrically conductive material, and is designed to dissipate or divert electrical energy induced by electromagnetic radiation.

The long, low-resistance structures depend on the function, and can be wires, for instance, which are a connection from poles or sensors located at or in the vicinity of the catheter tip to a plug connector located on the proximal catheter end. Such structures can also be metal braids or metal profiles, however, which are used to stiffen, shape, or torsionally stabilize the catheter.

The electrically conductive materials contained in the dissipation sleeve or the dissipation means could be conductive particles or materials, for instance, which are an extensive dissipation for the long, low-resistance structures of the deployment catheter, and/or which detune their antenna effect such that it is practically no longer present for the HF frequencies used in the MRI scanner (for example, 64 MHz for a 1.5T scanner, 128 MHz for a 3T scanner, etc.). Preferably, the electrically conductive material is a polymer matrix in which conductive particles are embedded, wherein the conductive particles preferably have an elongate shape, particularly preferably having a length-to-width or -diameter ratio greater than 2, and particularly preferably greater than 100. The polymer matrix preferably comprises silicone, polyurethane, and/or Peba (also known as "Pebax"), and the conductive particles preferably comprise carbon, particularly preferably carbon black and/or carbon fibers, carbon nanoparticles, metal-coated carbon particles, and/or carbon nanotubes, conductive carbon black, and/or metal particles.

According to another embodiment, the conductive material of the dissipation sleeve or the dissipation means can be formed of a metal, preferably a biocompatible metal. Particularly preferably the dissipation means is a metal braid, a metal coil, or a metal profile, wherein each of these stated dissipation means is embedded at least partially in the dissipation sleeve. The material of the dissipation sleeve of such braided, coil, or profiled tubes can also be non-conductive, as necessary.

According to a further embodiment, the dissipation sleeve and/or the dissipation means can be electrically coupled, at least in sections, galvanically or capacitively to the body tissue enclosing the dissipation device, to dissipate or divert the electrical energy induced by electromagnetic radiation to the surrounding body tissue. The energy absorbed in this manner is therefore given off to the body tissue by the dissipation sleeve or the dissipation means over a large surface area and without an undesired development of heat. This can be realized e.g., by using a partially exposed braid, or by a high particle density that extends to the surface. In the case of direct, galvanic contact with the body tissue, these materials or particles must be comprised of biocompatible substances such as, for example, carbon, gold, platinum, palladium, titanium, stainless steel, or the like.

In one embodiment of the sheath, the dissipation sleeve or the dissipation means are insulated from the body, i.e., it is electrically decoupled. In this embodiment, the dissipation device comprises a connecting means on the proximal end, which is electrically connected to the dissipation means to galvanically or capacitively dissipate or divert the electrical energy induced by electromagnetic radiation to an antipole located outside the body.

In order to perform their function, the sheaths according to the present invention are typically so long that they cover the majority of the deployment catheter. That is, typically only the part of the deployment catheter that is located in the handling region and is usually controllable or preformed extends out of the sheath. Since it is typically shorter than one-fourth of the wavelength of the HF frequency in the MRI scanner, the part of the deployment catheter extending out of the sheath does not function as an antenna for this frequency.

It is desirable, however, for the sheath or the dissipation device to have an adjustable length, e.g., because the deployment catheter or medical instruments are of different lengths, or because a longer extension of dissipation along the deployment catheter/medical instrument is desired. In this case, the dissipation sleeve or dissipation device comprises a first distal dissipation section and a second proximal dissipation section, wherein the second dissipation section is supported such that it is displaceable relative to the first section, in order to optimize the length of the dissipation device and, therefore, the protective length of the dissipation device such that the protective effect is maximized. To ensure that displacement and handling are simple in this configuration as well, the second dissipation section comprises a guide which displaceably guides the first dissipation section in a fluid-tight manner.

In an above-mentioned configuration of the dissipation device according to the present invention, in which the energy absorbed by the MR diagnostic device is diverted to an external antipole, the connecting means are on the proximal end of the second dissipation section, wherein said second dissipation means comprises an electrical connector preferably on the distal end thereof, which is suited for absorbing the energy absorbed by the first dissipation section, and likewise dissipating the same via the connecting means. The connector can be, for example, a plug contact, clamp contact, sliding contact, or similar solutions known to a person skilled in the art.

The antipole is used to dissipate or divert the energy absorbed by the dissipation device, or to compensate therefore using other suitable measures. The antipole is therefore a device for energy dissipation, which is preferably the shielding of the booth of the MR diagnostic device, the high-frequency shield of the scanner, the shield of an electrophysiological ablation device, or the potential of the neutral electrode of the electrophysiological ablation system. It is also possible for the device to be a combination of the aforementioned external devices. In addition, or as an alternative, to the stated devices, the connecting means can be electrically connected to a high-frequency generator, the amplitude and phase of which are adjustable, for compensating energy input. Furthermore, a matching network composed of RLC elements and/or transformers can be provided between the connecting means, the antipole, and/or the high-frequency generator, which ensures optimal dissipation or diversion of energy.

According to a further aspect of the present invention, and in an application of the dissipation device, the present invention comprises a system for treating the human body, which is comprised of a dissipation device of the aforementioned type, and an elongate medical instrument located temporarily in the body. Said instrument, which can also be an electrophysiological ablation catheter or a temporary cardial electrode or nerve line, comprises a first region which can be introduced into the human body and comprising a distal end, and a second region located outside of the body and comprising a proximal end, and comprises at least one galvanically conductive structure, wherein the medical instrument is displaceably supported in the dissipation device. The dissipation device is characterized in that it encloses the first region of the medical instrument at least in sections. The non-enclosed section of the medical instrument, i.e., the section located between the distal end of the instrument and the distal end of the dissipation device, has a length of less than ¼, and preferably less than ¹⁄₁₀ of the wavelength of the incident high-frequency wave coming from, for instance, an MR diagnostic device. This represents optimal protection of the medical instrument, since the antenna effect is particularly poor in such a section, as described above. However, since it must be ensured that the medical device is still functional, it is extremely important for the functional contact points to be flat in this section.

To ensure that no sections inadvertently result that are unprotected during the medical procedure, the dissipation device can preferably comprise a locking device which can be used to detachably lock the medical device, such that the medical instrument is prevented from being displaced in the dissipation device.

Furthermore, the medical instrument can comprise a temperature sensor on or in the vicinity of one of the electrical conductive structures thereof, and means are provided which act—with consideration for the temperature information delivered by said temperature sensor—on the high-frequency generator and/or the matching network such that the temperature increase above the body temperature is minimized. This temperature sensor or the means can also be designed such that they provide the user with indications regarding the length to set for the dissipation device in order to minimize the temperature increase above the body temperature.

The present invention is described in the following with reference to a plurality of embodiments and figures.

Figure 5:
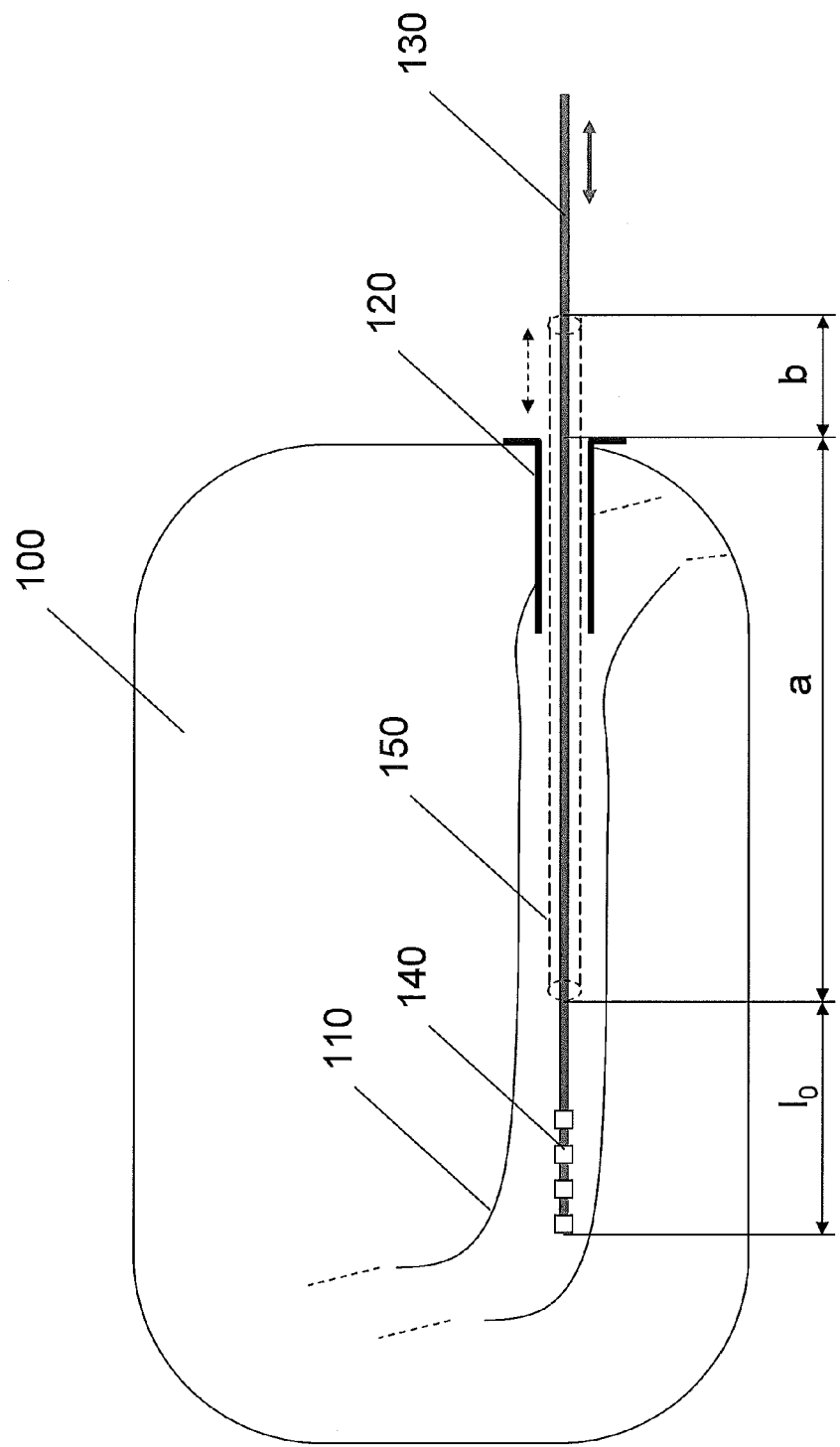
FIG. 5 shows a first embodiment of the inventive dissipation device, designed as a sheath for dissipating energy to the surrounding body tissue.

FIG. 5 shows a first simple embodiment of dissipation device 150 according to the present invention, and the system according to the present invention, comprising a deployment catheter 130 as the medical instrument. In this embodiment, the energy induced by the MR field is dissipated to the physical surroundings. The system is introduced into a body lumen, such as a blood vessel 110, of a human or animal body 100 using an introducer sheath 120. In this embodiment, the dissipation device 150 is a sheath in the form of a tube which is substantially cylindrical and is typically flexible (and is also referred to as a dissipation sleeve), through the lumen 110 of which the deployment catheter 130 is guided.

The dissipation sheath 150 according to the present invention is located in body 100 or body lumen 110 with a length a, and outside of the body 100 or blood vessel 110 with a length b. Preferably, length b is equal to 0. The distal end of the deployment catheter 130 extends with therapeutic or diagnostic catheter poles 140 out of the sheath by length $I_0$. In this case, length $I_0$ is preferably selected such that the largest possible section of deployment catheter 130 is covered by sheath 150, to provide the best possible protection against heating when the catheter is used safely. It must be ensured, however, that length $I_0$, i.e., the non-enclosed section of the medical instrument, between the distal end thereof and the distal end of the dissipation device, is less than ¼, and preferably less than ¹⁄₁₀ of the wavelength of an incident high-frequency wave.

Deployment catheter 130 and sheath 150 can be displaced relative to body 100 independently of one another. It is therefore possible to optimally adapt the protective region in which the sheath 150 encloses the application catheter 130. To ensure said optimal setting during the medical procedure, sheath 150 comprises a locking device which can be used to mechanically couple it to the catheter, to ensure that length $I_0$ remains constant (and as short as possible).

According to a further preferred embodiment, the tube of the dissipation device can comprise a first distal dissipation section and a second proximal dissipation section, wherein the second proximal dissipation section is supported such that it is displaceable relative to the first distal dissipation section—e.g. through a guide in the second proximal dissipation section, which guides the first distal dissipation section in a fluid-tight, displaceable manner—to optimize the length of the dissipation device and, therefore, the protective length of the dissipation device such that the protective effect is maximal. The total length of the sheath, comprised of lengths a and b, can therefore be varied using a telescope system.

The dissipation means in the tube of the sheath is comprised (at least in part) of electrically conductive materials. They are distributed homogeneously or heterogeneously in a carrier matrix (conductive plastic). The electrically conductive material can be, for example, a polymer matrix in which conductive particles are embedded, wherein the conductive particles preferably have an elongate shape, particularly preferably having a length-to-width or -diameter ratio greater than 2, and particularly preferably greater than 100. The polymer matrix preferably comprises silicone, polyurethane, and/or Peba (also known as "Pebax"), and the conductive particles comprise carbon, particularly preferably carbon black and/or carbon fibers, carbon nanoparticles, metal-coated carbon particles, and/or carbon nanotubes, conductive carbon black, and/or metal particles. One skilled in the art will appreciate, however, that other materials can be used without departing from the spirit and scope of the present invention. In a further embodiment, it is also possible to create the entire sheath out of one of these conductive materials.

According to another embodiment, the dissipation means of metallic conductive tracks, braids, coils, profiles or layers can be embedded in the plastic tube. Metallizations (or conductive layers) of the inner jacket surface and/or outer jacket surface of the tube are also present. In a particular embodiment, the layer is applied in a helical shape. The dissipation sleeve and/or the dissipation means of all aforementioned embodiments are electrically coupled, at least in sections, galvanically or capacitively to the body tissue surrounding the dissipation device, to dissipate or divert the electrical energy induced by electromagnetic radiation to the surrounding body tissue.

Figure 6:
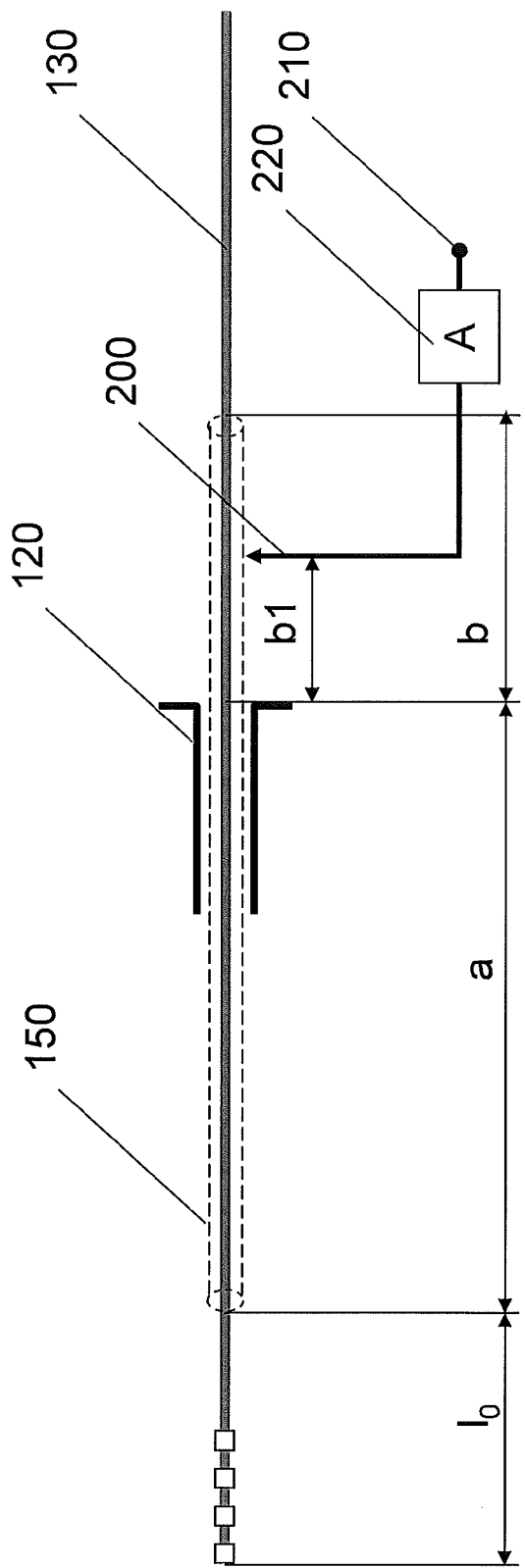
FIG. 6 shows a dissipation device according to an additional embodiment comprising a connecting means for dissipating the absorbed energy to an external opposite pole.

An exemplary aforementioned dissipation device and system are shown in FIG. 6. For this reason, the reference numbers are the same as in FIG. 5. Dissipation device 150, as shown, comprises an electrical connecting means 200 in the form of an electrical tap, which is electrically connected to the dissipation means in the tube or, if the tube itself is made of conductive material, to divert the dissipated energy outside of the body. The connecting means can establish the connection galvanically, e.g., by way of sliding contacts, a plug connection, or the like. The connecting means 200 can also bring about a capacitive coupling. Optimally, the connecting means 200 are situated at a distance b1 from the introducer sheath 120. In a special case, length b1 is equal to 0. The tap (connecting means 200) is then implemented at, or using, the introducer sheath which, in that case, comprises electrical contacts for contacting the dissipation device 150. In a further embodiment, the tap (connecting means 200) is always located on the end of the sheath, that is, b1 is equal to b.

Connecting means 200 establishes an electrical connection 210 to an antipole located outside of the body. Antipole 210 can be a device for dissipating energy, such as, for example, the shielding of the booth of an MR diagnostic device, the high-frequency shield of the scanner, the shield of an electrophysiological ablation device, the shield of the filter box between the ablator and patient, or the potential of the neutral electrode of the electrophysiological ablations system. In addition, or as an alternative, to electrical connection 210 to an antipole 210, the connecting means 200 can be electrically connected to a high-frequency generator, the amplitude and phase of which are adjustable, for compensating energy input. It is used for compensating energy input, wherein the high-frequency generator generates a high-frequency signal which corresponds to that of the particular scanner and is adjustable in terms of amplitude and phase. For phase-stable coupling to the high-frequency system of the MR device, said high-frequency generator has a phase-locked loop ("PLL").

Furthermore, the dissipation device according to the present invention can comprise a matching network 220 comprised of RLC elements and/or transformers between connecting means 200 thereof, electrical connection 210 of the antipole, and/or the high-frequency generator, said matching network 220 ensuring that energy dissipation or diversion is optimized.

Figure 7:
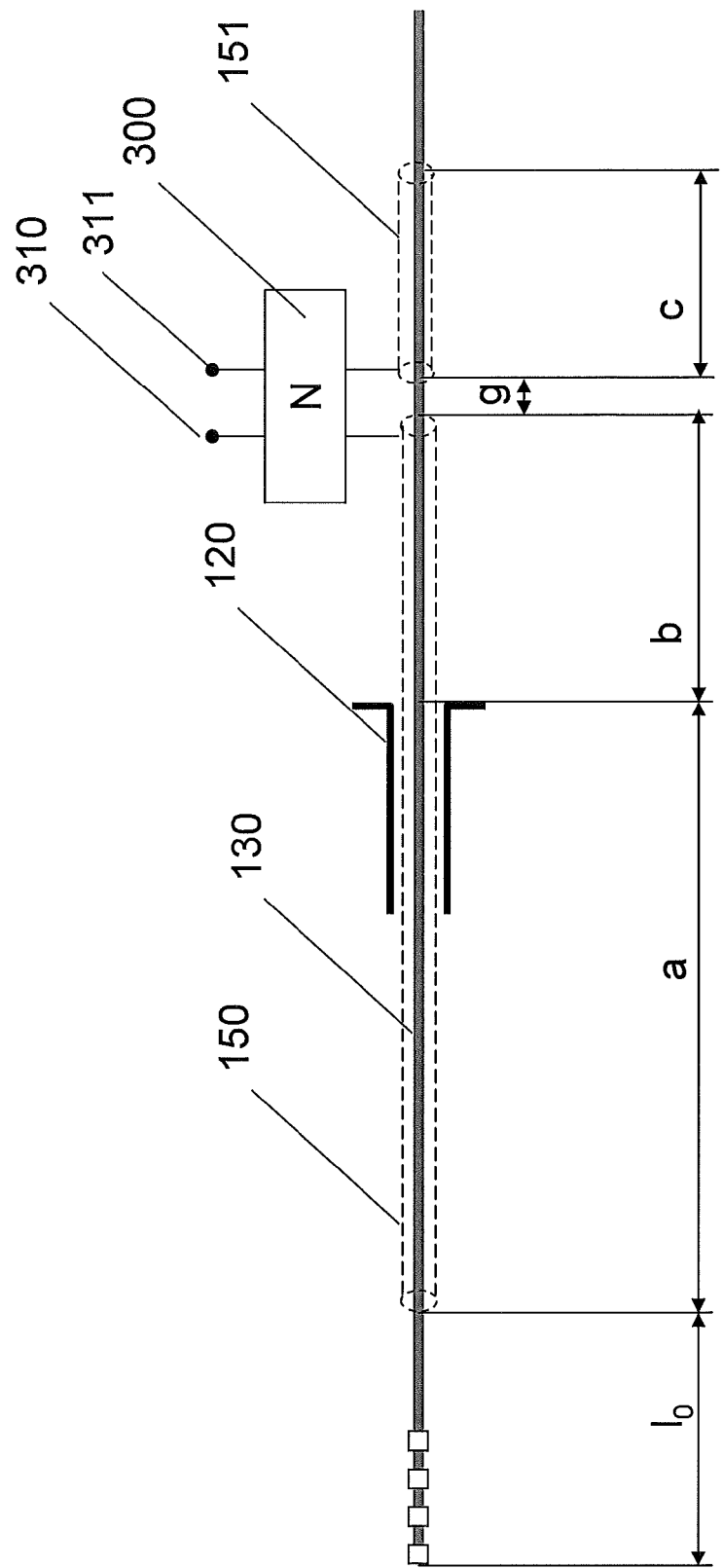
FIG. 7 shows a dissipation device according to a further embodiment for dissipating the absorbed energy to an external antipole, comprising a plurality of sheaths (sections).

FIG. 7 shows a further embodiment of the dissipation device comprising a second sheath section 151 having a length c with a gap having a length g toward the dissipating sleeve of dissipating device 150. The at least one second sheath 151 is installed downstream of dissipating device 150, wherein electrical networks 300 between each of said sheath (sections) 151 establish an electrical coupling of the dissipating device to the individual second sheath sections 151. Networks 300 are likewise provided with RLC elements and/or transformers, although they can also comprise waveguides. All of these components are adjustable.

Networks 300 couple the energy input of adjacent sheaths 150/151 such that the undesired heating of the catheter is prevented or reduced. Networks 300 also comprise connectors 310, 311 for energy dissipation or compensating energy input, comprising contacting means to antipoles or a connection of a generator, as described with reference to FIG. 6. Additional sheaths 151 can be displaced separately, and therefore the distance g is variable. Likewise, the lengths c of each sheath 151 are adjustable, being designed similar or identical to the above-mentioned telescope, for instance.

Additionally, each of the embodiments presented can comprise a unit 400 which is designed to ensure and optimize the detection and processing of sensor signals and the control of the above-mentioned variable components, such as, for example, adjustable antipoles, adjustable high-frequency generators 430, including PLLs, for the phase reference to the high-frequency system of the scanner, networks 220 and 300, and distances b, c and g.

Figure 8:
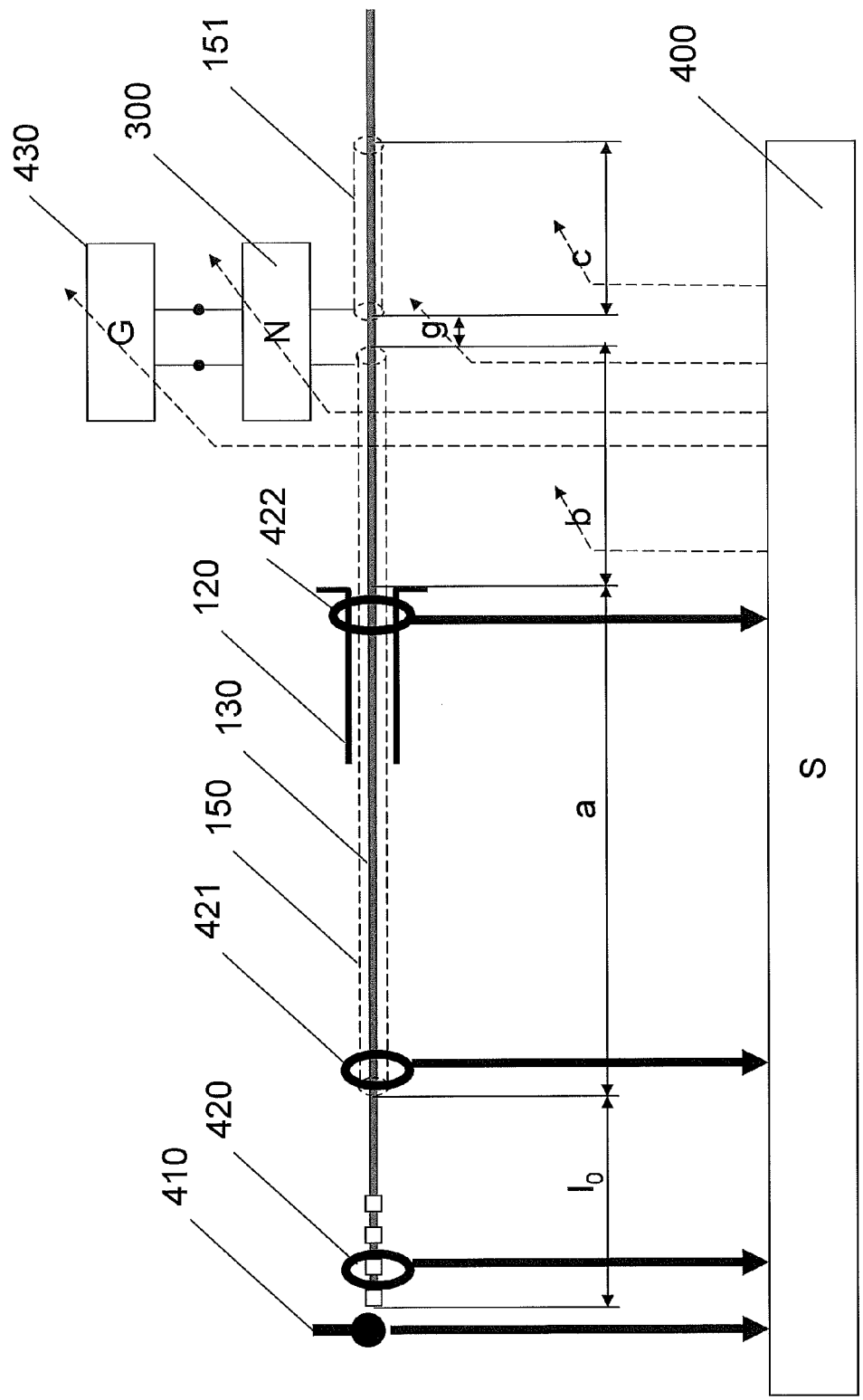
FIG. 8 shows dissipation device according to another embodiment comprising a unit for detecting and processing sensor signals.

For this purpose, as shown in FIG. 8, deployment catheter 130 and/or dissipation device 150 and/or sheath (sections) 151 and/or the sheaths are equipped with sensors 420, 421 or 422 which sense the effect of the energy input. The energy is expressed as a temperature increase at electrode poles 140 of deployment catheter 130, increased current flows through the lead of deployment catheter 130, and/or increased E fields. Sensors 420, 421 and 422 can therefore be temperature sensors (e.g., 410), B field/current flow sensors, or E field sensors. The sensors transmit their signals to a unit for detection and processing 400. The signals are conducted such that they are not interfered with by the fields of the scanner. Measures for this purpose include, for example, shields, optical/acoustic links, or radio at a frequency unknown to the scanner. Processing unit 400 then controls the aforementioned variable components in the set-up, such that heating or the causes thereof, i.e., current flow and E fields, are minimized. Processing unit 400 utilizes a controller for this purpose. The actuating elements are appropriate actuators (e.g., motors) which implement the necessary mechanical changes) or optical and/or acoustic displays which signal to the operator the direction in which the elements should be moved.

To support placement in the body, the dissipation device 150 is provided with means which make it visible in MRT imaging, for instance, by using a tracking coil or a contrast agent filling of the dissipation sleeve with gadolinium or gadolinium compounds, or superparamagnetic iron oxide particles.

The dissipation device 150 is pre-shaped in a suitable manner to stabilize the position of the deployment catheter 130 and reach the target sites that are relevant for therapy. Furthermore, dissipation device 150 can be provided with a slidable inner coating to support the manipulation of deployment catheter 130. To prevent image artifacts in MRT imaging, the electrically conductive parts—such as, the shield of dissipating device 150—are composed of materials having suitable magnetic susceptibility, in the distal region in particular. Suitable materials would be copper, aluminum, and/or graphite/carbon fibers, for instance.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE CHARACTERS

100: Human or animal body
110: Body lumen, in particular a blood vessel
120: Introducer sheath
130: Deployment catheter
140: Therapeutic or diagnostic catheter poles of the deployment catheter
150: Sheath (or "shielding device")
151: A second sheath having length c with a gap having length g from the first sheath ("shielding device")
200: Electrical tap ("connecting means") on the sheath at a distance b1 from the introducer sheath
210: Connection to an antipole, such as a device for energy dissipation or compensating energy input
220: Additional matching network
300: Coupling network N for coupling the shielding device and the second sheath
310, 311: Connectors for energy dissipation or compensating energy input comprising contacting means to antipoles
400: Unit for detecting and processing sensor signals and controlling the above-noted variable components in the set-up
410: Temperature sensor at the catheter poles of the deployment catheter
420-422: B field and/or E field sensors
430: Adjustable generator (including PLL for phase reference to the HF system of the scanner)

We claim:

1. A dissipation device having a proximal end, which is outside of the body, and a distal end, which is suited for elongate medical instruments placed temporarily in the body, the dissipation device comprising:
a plurality of dissipation sleeves, the combination of which extends from the proximal end to the distal end of the dissipation device, each of the dissipation sleeves separated by a gap;
a lumen which extends from the proximal end to the distal end, and in which the elongate medical instrument is displaceably guided for movement relative to the lumen as the medical instrument is inserted into and removed from the body, wherein the lumen is enclosed by the dissipation sleeve; and
electrical networks configured to establish electrical coupling of the dissipation device to each dissipation sleeve, wherein the electrical networks are located between each dissipation sleeve and are configured to couple energy input of adjacent dissipation sleeves,
wherein each dissipation sleeve is composed, at least partially, of electrically conductive material, such that each dissipation sleeve is designed to dissipate or divert electrical energy induced by electromagnetic radiation, and
wherein the dissipation device is usable with different elongate medical instruments.

2. The dissipation device according to claim 1, wherein the electrically conductive material is a polymer matrix in which conductive particles are embedded, and wherein the conductive particles have an elongate shape and a length-to-width or length-to-diameter ratio greater than 2.

3. The dissipation device according to claim 2, where the conductive particles have a length-to-width or length-to-diameter ratio greater than 100.

4. The dissipation device according to claim 2, wherein the polymer matrix comprises silicone, polyurethane, and/or Peba, and wherein the conductive particles comprise carbon, carbon black, carbon fibers, carbon nanoparticles, metal-coated carbon particles, carbon nanotubes, conductive carbon black, and/or metal particles.

5. The dissipation device according to claim 1, wherein at least one dissipation sleeve comprises a first distal dissipation section and a second proximal dissipation section, wherein the second proximal dissipation section is supported such that it is received in, and displaceable relative to, the first distal dissipation section in a telescoping configuration, in order to adjust the length of the dissipation device and, therefore, the protective length of the dissipation device such that the protective effect is maximized.

6. The dissipation device according to claim 5, wherein the second proximal dissipation section comprises a guide which displaceably guides the first distal dissipation section in a fluid-tight manner.

7. The dissipation device according to claim 1, wherein the conductive material is formed of a metal including a metal braid, a metal coil, or a metal profile, and wherein the conductive material is embedded at least partially in each dissipation sleeve.

8. The dissipation device according to claim 7, wherein the metal comprises a biocompatible metal.

9. The dissipation device according to claim 1, wherein at least one dissipation sleeve is electrically coupled, at least in sections, galvanically or capacitively to the body tissue enclosing the dissipation device, to dissipate or divert the electrical energy induced by electromagnetic radiation to the surrounding body tissue.

10. The dissipation device according to claim 1, wherein at least one dissipation sleeve is electrically decoupled, at least in sections, from the body tissue surrounding the dissipation device, and wherein the dissipation device comprises a connector on the proximal end, which is electrically connected to the dissipation sleeve to galvanically or capacitively dissipate or divert the electrical energy induced by electromagnetic radiation to an antipole located outside the body.

11. The dissipation device according to claim 10, wherein at least one dissipation sleeve comprises first and second dissipation sections, each having proximal and distal ends, wherein the connector is located on the proximal end of the second dissipation section, and wherein a second-connector is provided on the distal end of the second dissipation section, which is suited for absorbing the energy absorbed by the first dissipation section, and likewise dissipating the same via the connector.

12. The dissipation device according to claim 10, further comprising an antipole provided as a device for dissipating energy, wherein said device is provided for the shielding of the booth of the MR diagnostic device, the high-frequency shield of the scanner, the shield of an electrophysiological ablation device, or the potential of the neutral electrode of the electrophysiological ablation system.

13. The dissipation device according to claim 10, wherein the connector, provided in addition or as an alternative to the antipole, can be electrically connected to a high-frequency generator, the amplitude and phase of which is adjustable, for compensating energy input.

14. The dissipation device according to claim 13, wherein a matching network comprised of RLC elements or transformers or combinations thereof is provided between the connector, the antipole, or the high-frequency generator, or combinations thereof, which ensures the dissipation or diversion of energy is optimized.

15. A system for treating the human body, the system comprising a dissipation device according to claim 1, and an elongate medical instrument placed temporarily in the body, the elongate medical instrument comprising a first region which can be inserted into the human body, which has a distal end, and a second region which has a proximal end and is located outside the body, and comprising at least one galvanically electrically conductive structure, wherein the elongate medical instrument is displaceably supported in the dissipation device, and wherein the dissipation device encloses the first region of the medical instrument, at least in sections.

16. The system according to claim 15, wherein the non-enclosed section of the elongate medical instrument, between the distal end thereof and the distal end of the dissipation device, is less than ¼ of the wavelength of an incident high-frequency wave.

17. The system according to claim 15, wherein the non-enclosed section of the elongate medical instrument, between the distal end thereof and the distal end of the dissipation device, is less than 1/10 of the wavelength of an incident high-frequency wave.

18. The system according to claim 15, wherein the dissipation device further comprises a locking device which can be used to detachably lock the elongate medical instrument such that the elongate medical instrument is prevented from being displaced in the dissipation device.

19. A dissipation device having a proximal end, which is outside of the body, and a distal end, which is suited for elongate medical instruments placed temporarily in the body, the dissipation device comprising:

a plurality of dissipation sleeves configured for removable insertion into a person's body, the combination of which extends from the proximal end to the distal end of the dissipation device, each of the dissipation sleeves separated by a gap, at least one dissipation sleeve having a distal end which is received in the person's body and a proximal end which is disposed outside of the person's body when the distal end is received therein, and electrical networks configured to establish electrical coupling of the dissipation device to each dissipation sleeve, wherein the electrical networks are located between each dissipation sleeve and are configured to couple energy input of adjacent dissipation sleeves, wherein each dissipation sleeve is configured for receiving an elongate medical instrument while at least one dissipation sleeve is received inside the person's body such that the elongate medical instrument is displaceably guided by at least one dissipation sleeve for movement relative to at least one dissipation sleeve for temporary insertion in the person's body as the elongate medical instrument is inserted into and removed from the person's body, wherein each dissipation sleeve is composed, at least partially, of electrically conductive material, such that the dissipation sleeve is designed to dissipate or divert electrical energy induced by electromagnetic radiation, and wherein the dissipation device is usable with different elongate medical instruments.

20. The dissipation device according to claim 19, wherein at least one dissipation sleeve comprises a first distal dissipation section and a second proximal dissipation section, wherein the second proximal dissipation section is supported such that it is received in, and displaceable relative to, the first distal dissipation section in a telescoping configuration, in order to adjust the length of the dissipation device and, therefore, the protective length of the dissipation device such that the protective effect is maximized.

* * * * *